United States Patent
Knevels

(10) Patent No.: US 6,811,742 B2
(45) Date of Patent: Nov. 2, 2004

(54) SAMPLER FOR MELTS

(75) Inventor: Johan Knevels, Bree (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 0 days.

(21) Appl. No.: 10/256,898

(22) Filed: Sep. 27, 2002

(65) Prior Publication Data

US 2003/0062661 A1 Apr. 3, 2003

(30) Foreign Application Priority Data

Sep. 28, 2001 (DE) .......................................... 101 48 112

(51) Int. Cl.[7] .............................................. C21B 7/24
(52) U.S. Cl. .................................... 266/79; 73/DIG. 9
(58) Field of Search ........................ 266/79; 73/864.56, 73/864.53, DIG. 9

(56) References Cited

U.S. PATENT DOCUMENTS 3,321,978 A * 5/1967 Jackson ................... 73/864.53
5,057,149 A 10/1991 Conti et al.
6,370,973 B1 * 4/2002 Wunsch et al. .......... 73/864.53

FOREIGN PATENT DOCUMENTS

| DE | 7 405 180 U | 6/1974 |
| DE | 197 52 743 A1 | 6/1999 |
| EP | 1 126 036 A1 | 8/2001 |

* cited by examiner

Primary Examiner—Melvyn Andrews
(74) Attorney, Agent, or Firm—Akin Gump Strauss Hauer & Feld, L.L.P.

(57) ABSTRACT

A sampler for melts, in particular for slag, includes a body having an inlet and a sample chamber with an inlet opening. The inlet opening is located in a chamber wall delimited by a first metal plate with an opening. Removal of a sample from the sample chamber is simplified by arranging a second metal plate flat against the first metal plate, with the second metal plate having an opening that, together with the opening of the first metal plate, forms the inlet opening.

13 Claims, 3 Drawing Sheets

SAMPLER FOR MELTS

BACKGROUND OF THE INVENTION

This invention relates to a sampler for melts, in particular for slag, the sampler including a body having an inlet and a sample chamber with inlet opening, wherein the inlet opening is located in a chamber wall that is delimited by a first metal plate having an opening.

Samplers of this type are known from German published patent application DE 197 52 743 A1 and European published patent application EP 1 126 036 A1. Such samplers enable an effective removal of slag melt from a melt bath. With the known samplers, however, problems can occur in the removal of the sample from the sample chamber.

Other samplers are known from U.S. Pat. No. 5,057,149 and German utility model DE-GM 7 405 180. From U.S. Pat. No. 5,057,149 it is known to arrange a temporary protective cap, which is made of several layers that dissolve prior to or during entrance of the metal melt into the inlet channel of a sample chamber. Protective caps arranged in front of the inlet channel in a sample chamber are also known from DE-GM 7 405 180.

BRIEF SUMMARY OF THE INVENTION

An object of the present invention is to improve the known samplers and to simplify the removal of the sample from the sample chamber.

This object is achieved by the present invention by arranging a second metal plate flat against the first metal plate, with the second metal plate having an opening that, together with the opening in the first metal plate, forms the inlet opening, whereby the sample in the sample chamber is easily removed. The two metal plates lying against one another can move at least minimally with respect to one another. Moreover, the two metal plates lying against one another ensure a better heat insulation of the sample. A reduction in heat transport from the metal melt and away from the sample chamber and the sample itself leads to less sticking of the sample to the metal plate surrounding the inlet opening.

Beneficially, the form and size of the openings of the two metal plates are the same, and the two openings are preferably centrally located. This allows the melt to flow into the sample chamber evenly and without additional eddy formation. Advantageously, the metal plates are made of steel. They are each approximately 1 mm thick.

The sample chamber is advantageously designed as a flat sample chamber, wherein the wall of the sample chamber opposite the inlet opening can be formed by another metal plate, in particular a steel plate, and wherein the flat sample chamber can have a lateral perimeter wall bordering the metal plate. This wall can likewise be made of metal, in particular steel. The perimeter wall can have an annular circumferential groove on its surface facing the sample chamber.

It is advantageous if a pre-chamber is arranged in the body in front of the two metal plates with the openings. The slag is collected in this pre-chamber prior to flowing into the sample chamber. The pre-chamber can be designed in the shape of a funnel, i.e., it has at its end opposite the inlet opening a larger cross sectional area than at the end facing the inlet opening. The larger cross sectional area opposite the inlet opening is thereby designed as the opening for taking the sample (sample-taking opening).

Beneficially, the body surrounding the sample chamber and the pre-chamber is made of foundry sand. The body can either be arranged on a carrier, so that the sampler is used as an immersion sampler, or it can have a placement surface on its end opposite the sample-taking opening, or it can be held in a known manner such that the sample-taking opening forms the upper closure of the body. In this case, a slag sample can be poured from above into the pre-chamber. It then runs from above into the sample chamber.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF THE INVENTION

Figure 1:
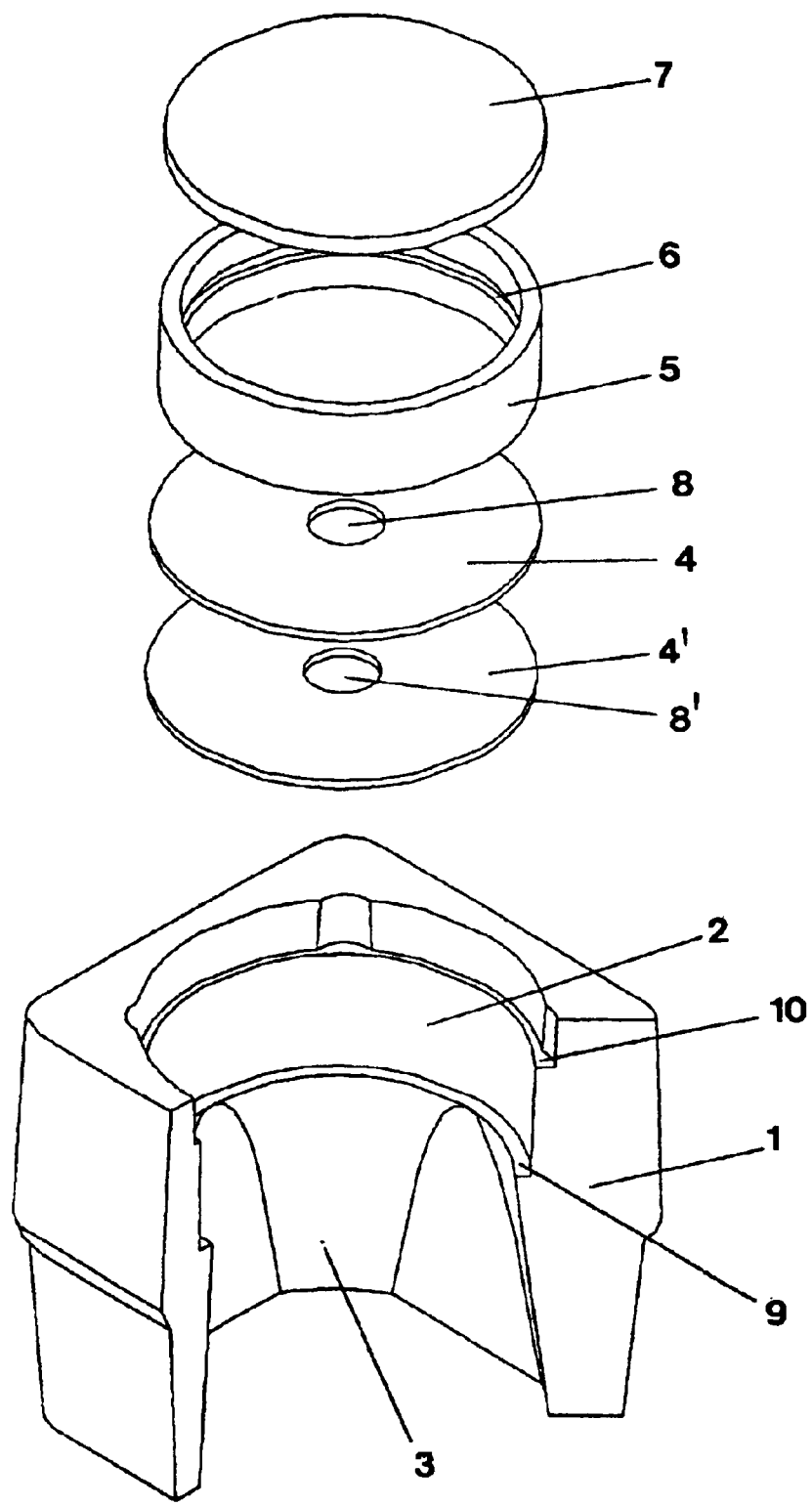
FIG. 1 is an exploded, perspective view, partially in section, showing the individual parts of a sampler according to the invention.
Figure 2:
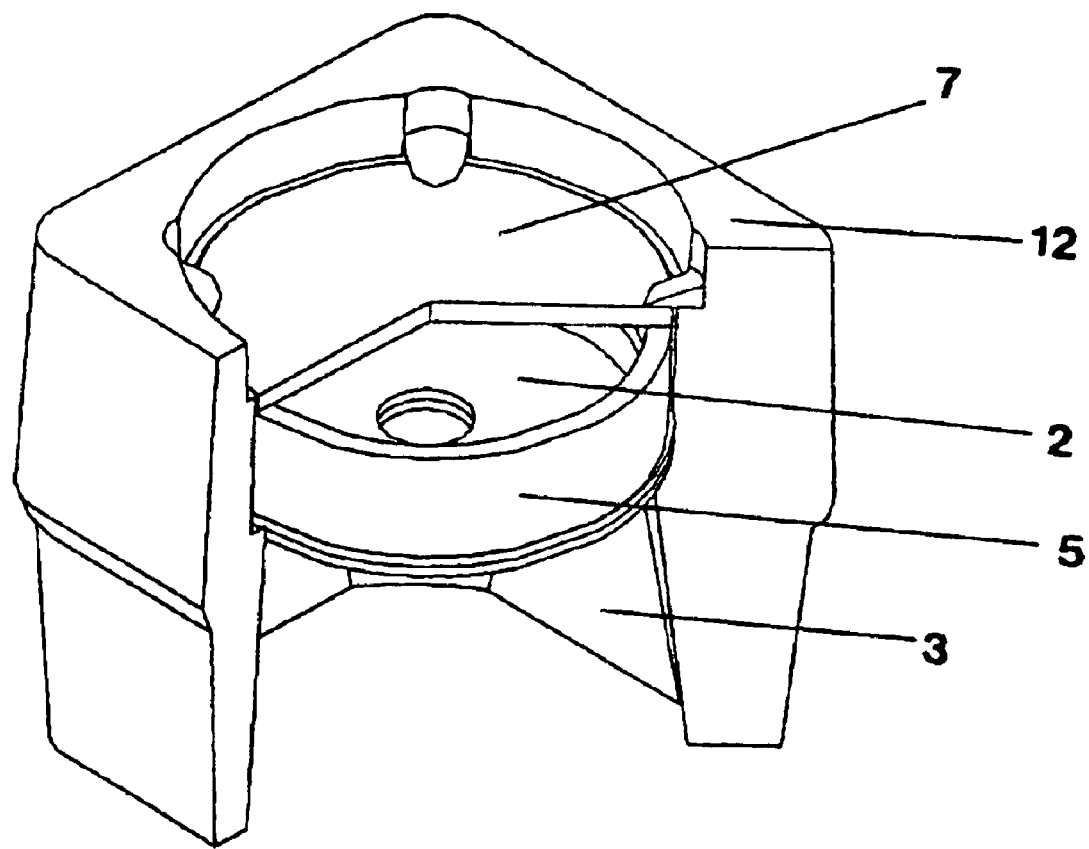
FIG. 2 is a sectioned perspective view, similar to FIG. 1, but showing the parts of the sampler installed.
Figure 3:
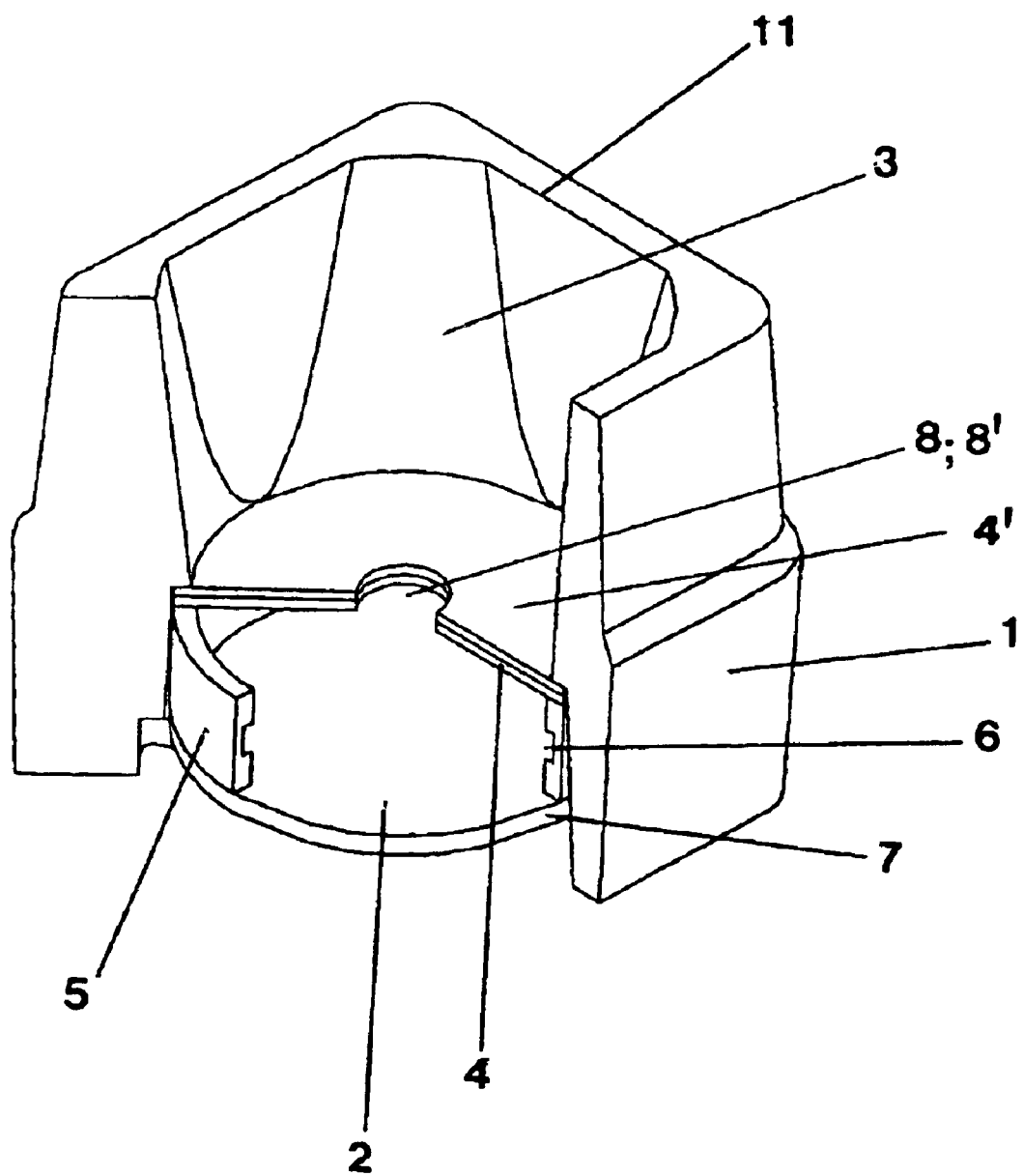
FIG. 3 is a sectioned, perspective view of sampler shown in its operating position.

The body 1, made of foundry sand, has a sample chamber 2 for forming flat samples and a funnel-shaped pre-chamber 3. The sample chamber 2 is delimited from the pre-chamber 3 by a first metal plate 4 and a second metal plate 4'. Laterally, the sample chamber 2 is delimited by a perimeter wall 5 formed by a steel ring, which has an annular groove 6 around its inner surface. The third metal plate 7, which is arranged opposite the two metal plates 4, 4' forms the closure of the sample chamber. In each of the metal plates 4, 4' is provided a respective opening 8, 8' that is centrally located and is formed as circular bore. The openings 8, 8' together form the inlet opening into the sample chamber 2.

The assembly of such a sampler is relatively simple. The individual parts are simply inserted into the body from one side, with the metal plates 4; 4' and 7 each lying on an annular supporting shoulder 9, 10. The metal plates 4' 7 lie against the perimeter wall 5.

The pre-chamber 3 has its largest cross sectional area at its end 11 lying opposite the inlet opening. The melt can be poured from above into the funnel formed thereby, using a ladle, into the pre-chamber 3, while the body 1 stands with its support surface 12 resting on a refractory base.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

I claim:

1. A sampler for melts, comprising a body (1) having an inlet and a sample chamber (2) formed by walls, the sample chamber (2) having an inlet opening arranged in one of the chamber walls, the one chamber wall being delimited by a first metal plate (4) having a first opening (8) and a second metal plate (4') having a second opening (8'), the second metal plate (4') being arranged flat against the first metal plate (4), such that the first and second openings (8, 8') together form the inlet opening.

2. The sampler according to claim 1, wherein the first and second openings (8; 8') have the same shape and size.

3. The sampler according to claim 1, wherein the first and second metal plates (4; 4') comprise steel.

4. The sampler according to claim 1, wherein the sample chamber (2) has a form of a flat sample chamber.

5. The sampler according to claim 4, wherein a wall of the sample chamber (2) lying opposite the inlet opening comprises a third metal plate (7).

6. The sampler according to claim 5, wherein the third metal plate (7) comprises steel.

7. The sampler according to claim 5, wherein the flat sample chamber has a lateral perimeter wall (5) bordering against the metal plates (4; 7) and made of metal.

8. The sampler according to claim 7, wherein the lateral perimeter wall (5) comprises steel.

9. The sampler according to claim 7, wherein the lateral perimeter wall (5) has an annular groove (6) on its surface facing the sample chamber (2).

10. The sampler according to claim 1, further comprising a pre-chamber (3) arranged in the body (1) in front of the two metal plates (4; 4').

11. The sampler according to claim 10, wherein the pre-chamber (3) has a larger cross sectional area at its first end (11) lying opposite the inlet opening than at its second end facing the inlet opening.

12. The sampler according to claim 11, wherein the pre-chamber (3) has a sample-taking opening formed by the larger cross sectional area.

13. The sampler according to claim 1, wherein the body (1) comprises foundry sand.

* * * * *